United States Patent
Nikolayev et al.

(10) Patent No.: US 10,910,701 B2
(45) Date of Patent: Feb. 2, 2021

(54) LOW-PROFILE, IMPEDANCE-ROBUST RADIO ANTENNA

(71) Applicants: BODYCAP, Herouvile Saint Clair (FR); CENTRE NATIONAL DE LA RECHERCHE SCIENTIFIQUE, Paris (FR); UNIVERSITE DE RENNES 1, Rennes (FR)

(72) Inventors: Denys Nikolayev, Rennes (FR); Maxim Zhadobov, Betton (FR); Ronan Sauleau, Acigné (FR)

(73) Assignees: BODYCAP, Herouville Saint Clair (FR); CENTRE NATIONAL DE LA RECHERCHE SCIENTIFIQUE, Paris (FR); UNIVERSITE DE RENNES 1, Rennes (FR)

( * ) Notice: Subject to any disclaimer, the term of this patent is extended or adjusted under 35 U.S.C. 154(b) by 0 days.

(21) Appl. No.: 16/651,976

(22) PCT Filed: Oct. 4, 2018

(86) PCT No.: PCT/FR2018/052442
§ 371 (c)(1),
(2) Date: Mar. 27, 2020

(87) PCT Pub. No.: WO2019/069024
PCT Pub. Date: Apr. 11, 2019

(65) Prior Publication Data
US 2020/0266528 A1    Aug. 20, 2020

(30) Foreign Application Priority Data

Oct. 4, 2017   (FR) ..................................... 17 59267

(51) Int. Cl.
*G08B 1/08*     (2006.01)
*H01Q 1/27*     (2006.01)
(Continued)

(52) U.S. Cl.
CPC .............. *H01Q 1/273* (2013.01); *A61B 5/073* (2013.01); *A61B 5/076* (2013.01); *G08C 17/02* (2013.01); *H01Q 1/38* (2013.01); *H01Q 1/48* (2013.01)

(58) Field of Classification Search
CPC . H01Q 1/273; H01Q 1/48; H01Q 1/38; G08C 17/02; A61B 5/076; A61B 5/073
(Continued)

(56) References Cited

U.S. PATENT DOCUMENTS 6,515,629 B1   2/2003   Kuo et al.
2010/0149042 A1   6/2010   Utsi et al.
(Continued)

FOREIGN PATENT DOCUMENTS

CN       105870602 A       8/2016
KR       20140119606 A   * 10/2014
(Continued)

OTHER PUBLICATIONS

Search Report dated Dec. 4, 2018 for PCT Application No. PCT/FR2018/052442.
(Continued)

*Primary Examiner* — Tanmay K Shah

(57) ABSTRACT

The radio antenna comprises a substrate formed of a dielectric material; a ground plane made of an electrically conductive material, the ground plane being arranged on a first face (F2) of the substrate; a resonator configured to convert an incident electrical signal into an electromagnetic wave. The resonator includes a first element (E1) having a first characteristic impedance and a second element (E2) having a second characteristic impedance that is higher than the first characteristic impedance. The first element (E1) is configured to receive the incident electrical signal, the first element (E1) is formed by a strip of electrically conductive material, (Continued)

Figure 1:
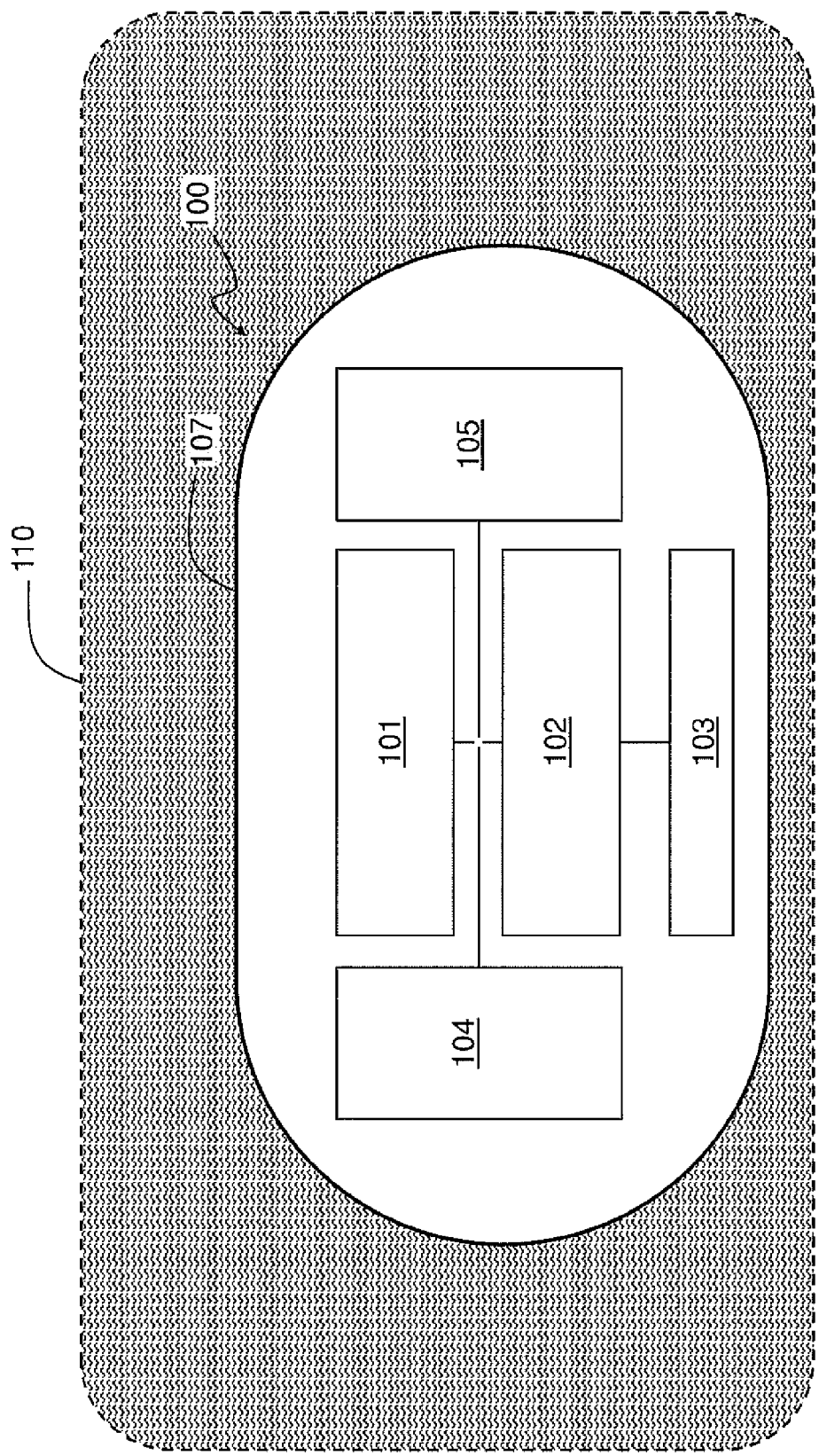

the strip being arranged on a second face (F1) of the substrate opposite the first face (F2). The second element (E2) is formed by a rectilinear segment, cut in the ground plane and separated from the rest of the ground plane by a slot (202) of fixed width. The second element (E2) is electrically connected to the ground plane at a first end of the segment and electrically connected to the first element at a second end of the segment by means of a via (210) passing through the substrate.

19 Claims, 4 Drawing Sheets

(51) Int. Cl.
    *A61B 5/07*     (2006.01)
    *G08C 17/02*     (2006.01)
    *H01Q 1/38*     (2006.01)
    *H01Q 1/48*     (2006.01)

(58) Field of Classification Search
    USPC .................................................... 340/539.12
    See application file for complete search history.

(56) References Cited

U.S. PATENT DOCUMENTS

| | | |
|---|---|---|
| 2012/0280885 A1 | 11/2012 | Arai et al. |
| 2014/0152514 A1 | 6/2014 | Vilenskiy et al. |
| 2016/0006215 A1* | 1/2016 | Koyama ................. H01P 3/121 372/45.01 |
| 2017/0117620 A1* | 4/2017 | Lapushin ................. H01Q 1/38 |

FOREIGN PATENT DOCUMENTS

| | | |
|---|---|---|
| KR | 20140119606 A | 10/2014 |
| WO | WO2011111008 A1 | 9/2011 |

OTHER PUBLICATIONS

Sumin Yun et al., "Outer-Wall Loop Antenna for Ultrawideband Capsule Endoscope System", IEEE Antennas and Wireless Propagation Letters, 2010, pp. 1135-1138, vol. 9.

* cited by examiner

LOW-PROFILE, IMPEDANCE-ROBUST RADIO ANTENNA

CROSS-REFERENCE TO RELATED APPLICATIONS

The application is a National Phase of International Application PCT/FR2018/052442 filed on Oct. 4, 2018, which claims priority to French Patent Application No. 1759267, filed on Oct. 4, 2017, in the French Intellectual Property Office, the disclosures of each of which are incorporated herein by reference.

FIELD OF THE INVENTION

The present description relates to a radio antenna and a biotelemetry device equipped with such a radio antenna.

STATE OF THE ART

In the field of medical applications, biotelemetry devices are used for the acquisition of physiological signals and the analysis of associated physiological data.

Among the biotelemetry devices, there are ingestible and/or implantable in vivo biotelemetry devices, which can be used both for the collection of physiological signals and the implementation of therapeutic functions, such as for example drug delivery or electrical stimulation. These biotelemetry devices are for example in the form of ingestible capsules or implants which can be inserted into the body of humans or animals.

These biotelemetry devices incorporate a radio antenna configured to transmit and/or receive an electromagnetic wave.

The radio antenna is used to transmit data to, or receive instructions from, external data control/analysis equipment. This external equipment is used in particular to analyze ex vivo the data transmitted by the radio antenna.

When the biotelemetry device is placed in a surrounding medium (for example a biological medium), the antenna is strongly coupled with this surrounding medium and the impedance of the radioelectric antenna is thus strongly dependent on the electromagnetic properties (permittivity, conductivity) of this surrounding environment. In particular, a mismatch of the radio antenna with respect to the microcontroller can occur due to the electromagnetic properties of the surrounding medium.

Patent application WO2010/119207A1 discloses an example of a radio antenna, comprising a resonator in the form of an electrically conductive flat body, comprising two elements of distinct characteristic impedances, a first element being formed by a strip of conductive material and the second element being formed by a serpentine with one or more elbows. In this example, the two elements of the flat body are of the microstrip type close to the surrounding medium. The characteristic impedances of these two elements are therefore likely to be affected by the variable electromagnetic properties of the surrounding environment in which this radio antenna is used.

Such a radio antenna thus has a strong coupling with the surrounding medium and its impedance is therefore appreciably affected by the surrounding medium. Such a radio antenna therefore lacks versatility in that when the radio antenna is designed for a specific surrounding environment, it can malfunction when it is in another surrounding environment. This is particularly troublesome in the context of the use of these radio antennas in an ingestible and/or implantable in vivo biotelemetry device intended to be in contact with various surrounding biological media.

An impedance mismatch between the radio antenna and the microprocessor further induces energy losses in the biotelemetry device and impacts the transmission performance of the radio antenna, in particular the power of the emitted electromagnetic wave. This is all the more problematic since the electromagnetic wave must, in order to reach the external equipment, pass through the body into which the biotelemetry device has been introduced, with thicknesses and types of tissue to be crossed which can be variable depending on the location in the body of the biotelemetry device.

There thus appears a need for a radio antenna that is robust in impedance and not very sensitive to variations in the electromagnetic properties of the surrounding medium, which can be used in an ingestible and/or implantable in vivo biotelemetry device, intended to pass through biological media with various electromagnetic properties.

SUMMARY

The present description relates, according to a first aspect, to a radio antenna. The radio antenna includes: a substrate formed of a dielectric material; a ground plane of electrically conductive material, arranged on a first face of the substrate; a resonator configured to convert an incident electrical signal into an electromagnetic wave, the resonator comprising a first element having a first characteristic impedance and a second element having a second characteristic impedance greater than the first characteristic impedance. The first element is configured to receive the incident electrical signal, the first element is formed by a strip of electrically conductive material, the strip being arranged on a second face of the substrate opposite to the first face. The second element is formed by a rectilinear segment, cut in the ground plane and separated from the rest of the ground plane by a slot of substantially fixed width. The second element is electrically connected to the ground plane at a first end of the segment and electrically connected to the first element at a second end of the segment by means of a via passing through the substrate.

The radio antenna according to the first aspect comprises both a coplanar element, in the ground plane, and an element in the form of a strip of electrically conductive material (produced for example, according to the so-called microstrip technology).

Because the second element is formed by a rectilinear segment, the circulation of electric currents in this element is channeled in the direction of this segment, which avoids losses related to the polarization impurity.

Such a radio antenna is robust in impedance also due to the combined use of microstrip technology and coplanar technology.

Because of the two faces of the radio antenna, the radio antenna can be placed so that the first face comprising the first element is on the side of a surrounding medium and that the second element is on the side opposite to the surrounding medium. The variation of the electromagnetic properties of the surrounding medium will mainly impact the characteristic impedance of the first element. In addition, the second element with higher characteristic impedance is better decoupled and isolated from this surrounding medium, since this second element is produced as a coplanar line in the ground plane of the antenna.

In one or more embodiments, the width of the slit between the rectilinear segment and the ground plane is comparable to or less than the distance between the rectilinear segment and the surrounding medium, which makes it possible to "constrain" the non-propagating electric field inside the substrate and therefore reducing the sensitivity of the second element to variations in the electromagnetic properties of the surrounding medium.

Thus the characteristic impedance of the radio antenna will be little affected by the surrounding medium or the change in the surrounding medium or to variations in the different electromagnetic properties of the surrounding medium, because the effect on the impedance of the radio antenna will be limited to the effect on the characteristic impedance of the first element. All this contributes to increasing the impedance robustness of the radio antenna and to reducing the losses by default of impedance matching between the radio antenna and the rest of the electronic circuit in the biotelemetry device. The antenna impedance is not very sensitive to variations in the surrounding environment. The reflection coefficient $S_{11}$, determined as the complex ratio between the complex intensity of the incident electrical signal converted by the antenna into an electromagnetic wave and the complex intensity of the reflected electrical signal resulting from a reflection of a fraction of the incident electrical signal, is such that $|S_{11}|<-10$ dB in a whole range of surrounding media.

It is therefore possible to use such a radio antenna for the production of an ingestible and/or implantable biotelemetry device in vivo intended to be in contact with various surrounding biological media (for example, human and/or animal body tissue) and/or for multiple application scenarios.

Such an antenna lends itself to being produced in a printed circuit and can also be integrated into a biotelemetric capsule.

Such a radio antenna is also suitable for making a miniature radio antenna, for example with a substrate thickness of less than 1 mm and a substrate width/length of less than 3 cm, and can therefore easily be integrated into a biotelemetry device such as a biotelemetric capsule. This antenna is a low profile antenna, the thickness of the antenna being negligible compared to its size. Such an antenna occupies a negligible space in a biotelemetric capsule, allows a high degree of miniaturization while having increased efficiency in transmission.

Such a radio antenna can also be produced on a flexible substrate, so as to be able to conform to the interior surface of a biotelemetry device such as a capsule.

In one or more embodiments of the radio antenna according to the first aspect, the rectilinear segment is oriented in a first direction and the strip of conductive material extends longitudinally in a second direction distinct from the first direction.

In one or more embodiments of the radio antenna according to the first aspect, the first direction is substantially perpendicular to the second direction.

In one or more embodiments of the radio antenna according to the first aspect, the strip of conductive material is of parallelepiped, serpentine or zigzag shape.

In one or more embodiments of the radio antenna according to the first aspect, the rectilinear segment is oriented in a first direction and the strip of conductive material extends longitudinally in a second direction distinct from the first direction, wherein the resonance frequency fres of the radio antenna is related to the lhigh dimension in the first direction of the straight segment and the llow dimension in the first direction of the strip of conductive material, to the characteristic impedance Zc-low of the first element and to the characteristic Zc-high impedance of the second element by the relations:

$$-Z_{c\text{-}low}+Z_{c\text{-}high}\tan(\beta_{high}l_{high})\tan(\beta_{low}l_{low})=0$$

$$Z_{c\text{-}high}\tan(\beta_{low}l_{low})+Z_{c\text{-}low}\tan(\beta_{high}l_{high})\neq 0$$

$\beta_{low}$ being the phase constant of the first element defined by:

$$\beta_{low}=(2\pi)/cf_{res}\sqrt{\in_{low}^{r,\mathit{eff}}}$$

Where $\beta_{high}$ is the phase constant of the second element defined by $$\beta_{high}=(2\pi)/cf_{res}\sqrt{\in_{high}^{r,\mathit{eff}}}$$

c being the speed of light, $\in_{high}^{r,\mathit{eff}}$ being the effective relative permittivity of the second element, $\in_{low}^{r,\mathit{eff}}$ being the effective relative permittivity of the first element.

In one or more embodiments of the radio antenna according to the first aspect, the ratio between the maximum width of the strip of conductive material and the width of the straight segment is between 5 and 0.2.

The characteristics of the various embodiments of the radio antenna according to the first aspect can be combined with one another.

The present description relates, according to a second aspect, to a biotelemetry device comprising a radio antenna according to the first aspect. The characteristics, properties, advantages and/or effects of the radio antenna according to the first aspect can be transposed directly to the biotelemetry device according to the second aspect.

In one or more embodiments of the biotelemetry device according to the second aspect, the substrate being in a flexible material and the biotelemetry device being in the form of a capsule in which the substrate is rolled so that the first face of the substrate is turned towards the inside the capsule and the second face is turned towards the outside of the capsule.

In one or more embodiments of the biotelemetry device according to the second aspect, the substrate of the radio electric antenna is a flexible polyimide substrate conforming to the internal surface of the capsule.

In one or more embodiments of the biotelemetry device according to the second aspect, the substrate is in a rigid material and of cylindrical shape, the biotelemetry device being integrated in a capsule in which the radio antenna is placed that the first face of the substrate is facing the inside of the capsule and the second face is facing the outside of the capsule.

BRIEF DESCRIPTION OF THE FIGS

Figure 2A:
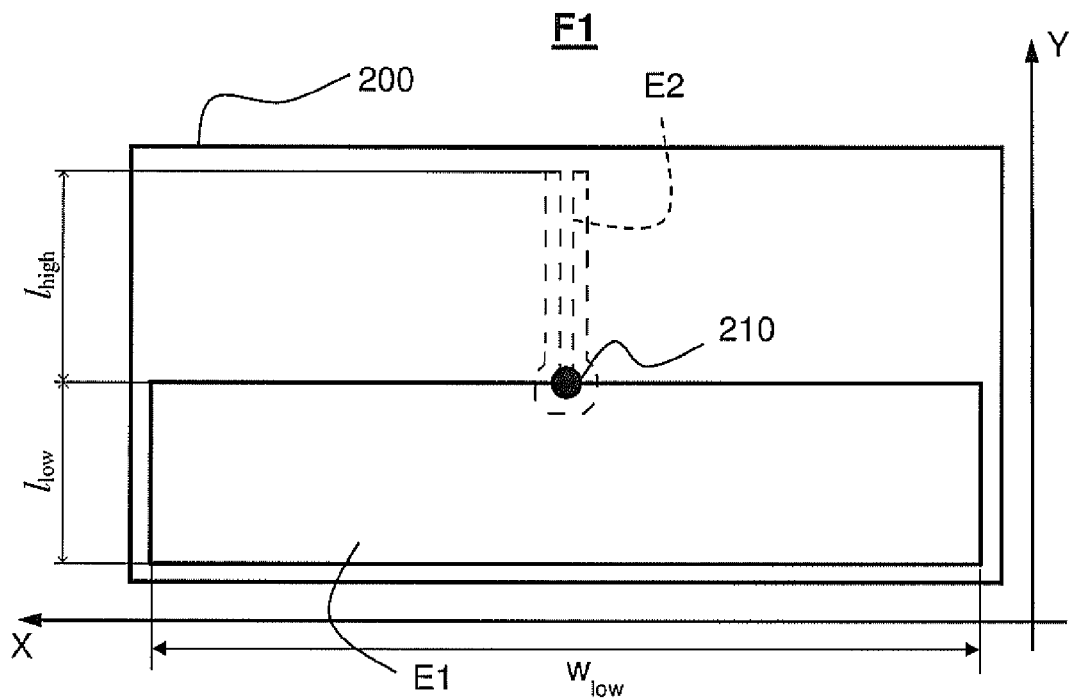
Figure 2B:
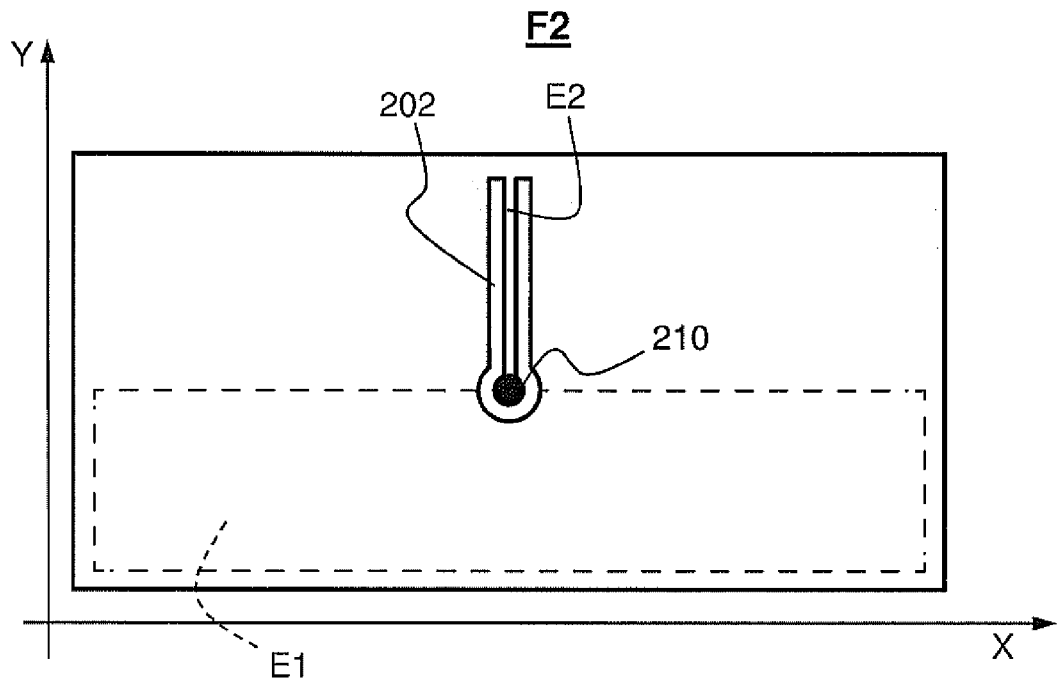
Figure 3:
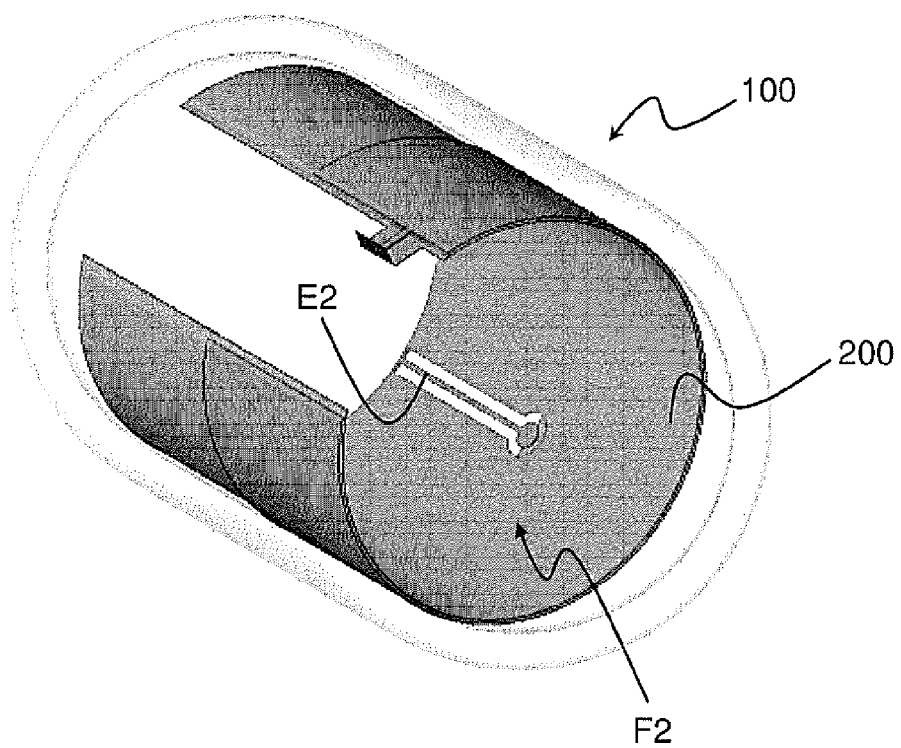
Figure 4:
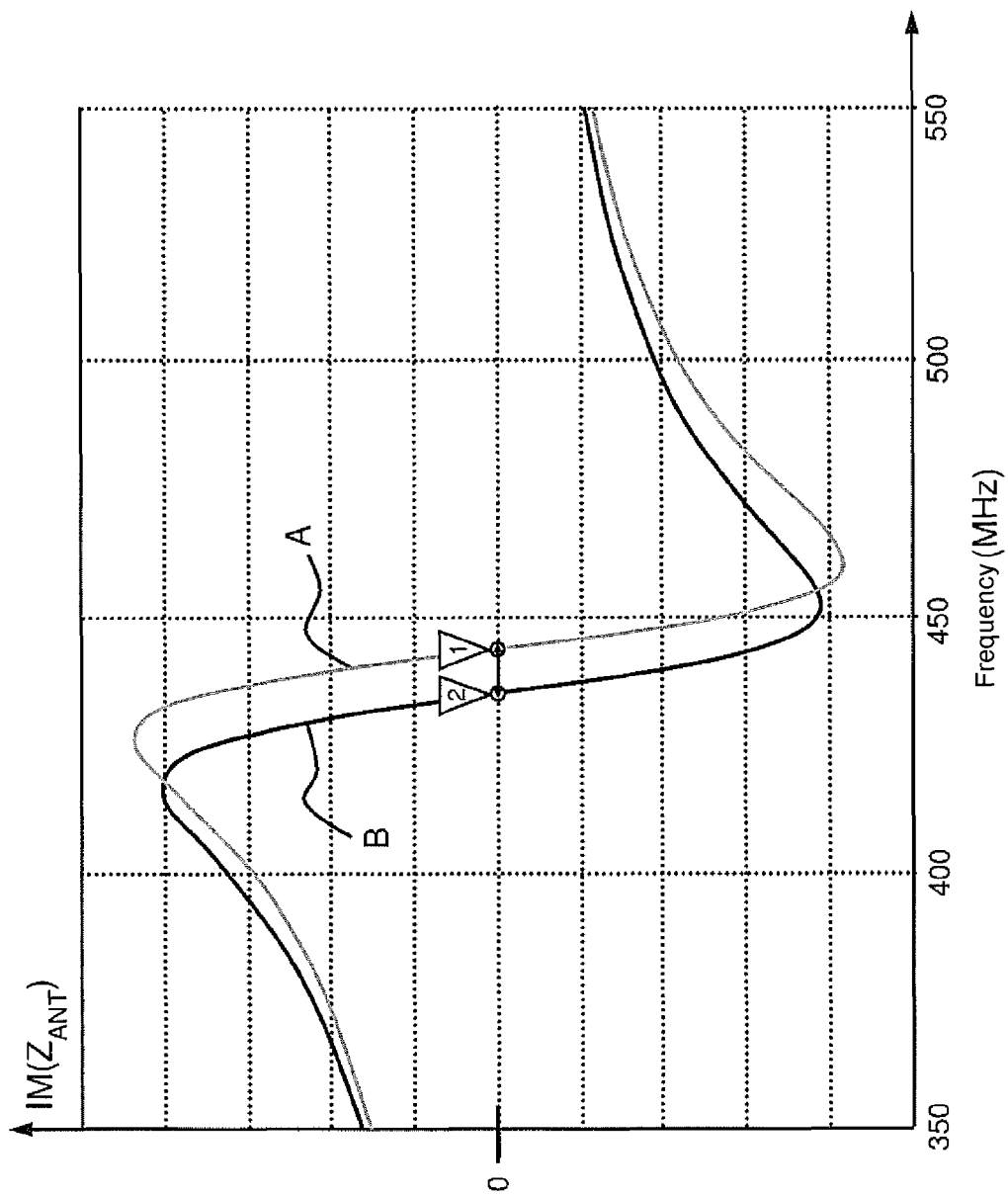

Other advantages and characteristics of the technology presented above will appear on reading the detailed description below, made with reference to the FIGS. in which:

FIG. 1 schematically represents a biotelemetry device according to an exemplary embodiment;

FIGS. 2A and 2B schematically represent a radio antenna according to an exemplary embodiment;

FIG. 3 schematically represents a biotelemetry device according to an exemplary embodiment;

FIG. 4 illustrates aspects of the operation and performance of a radio antenna according to an exemplary embodiment.

In the various embodiments which will be described with reference to the FIGS., similar or identical elements have the same references.

DETAILED DESCRIPTION

The various embodiments and aspects described below can be combined or simplified in many ways.

Only certain embodiments of examples are described in detail to ensure the clarity of the description, but these examples are not intended to limit the general scope of the principles emerging from this description considered as a whole.

FIG. 1 schematically shows an example of a biometric device 100, in the form of an ingestible capsule.

The biotelemetry device 100 comprises a microcontroller 101, a radio frequency circuit 102, a radio antenna 103, a power source 104. Optionally, the biotelemetry device 100 may include an additional circuit 105, for example a biomedical application circuit or a sensor.

In one or more embodiments, the power source 104 is configured to electrically power the microcontroller 101, the radio frequency circuit 102, the radio antenna 103 and the additional circuit 105.

In one or more embodiments, the radio antenna 103 is configured to communicate via a radio link with an external device (not shown), the radio antenna 103 can for example transmit data (for example biotelemetry data acquired by the biotelemetry device 100) to the external device and receive data (for example operational instructions and/or therapeutic treatment) from such an external device.

In one or more embodiments, the radio antenna can transmit and receive electromagnetic waves at high frequencies, for example in the range of $10^8$ Hz to $10^{10}$ Hz.

According to one or more embodiments, the microcontroller comprises an electrical signal generation unit 112 configured to generate the incident electrical signal. According to one or more embodiments, the microcontroller comprises a data processing unit 113.

In one or more embodiments, the microcontroller 101 is configured to generate an incident electrical signal to be converted into an electromagnetic wave by the radio antenna and/or to amplify a signal received from the radio antenna.

In one or more embodiments, the microcontroller 101 is configured to process data, for example to process the data received by the radio antenna 103 or data acquired by the additional circuit 105.

In one or more embodiments, all of the components of the biotelemetry device 100 (the microcontroller 101, the radio frequency circuit 102, the radio antenna 103, the power source 104 and optionally, the an additional circuit 105) is integrated in a biocompatible capsule 107.

In one or more embodiments, the radio frequency circuit 102 is interconnected between the microcontroller 101 and the radio antenna 103. The radio frequency circuit 102 serves as an electrical interface between the microcontroller 101.

In one or more embodiments, the biomedical application circuit 105 is configured to implement diagnostic functions and/or therapeutic functions. The diagnostic functions may include functions for acquiring or measuring diagnostic data, for example by means of one or more sensors, such as for example, temperature sensors, electronic sensors, MEMS ("Microelectromechanical Systems") or micro fluidics sensors. Diagnostic functions may include endoscopy, image acquisition, glucose or other physiological parameters, antibody detection, etc. Therapeutic functions may include for example drug delivery and electrical stimulation, for example nerve stimulation.

The biotelemetry device 100 is intended to be used in a surrounding medium 110, for example after ingestion or implantation in vivo. As the biotelemetry device 100 moves through the human body, for example during gastrointestinal transit, this surrounding medium 110 is likely to have various properties.

The electromagnetic (EM) properties of the surrounding medium 110 surrounding the biotelemetry device 100 determines the coupling between the radio antenna 103 and the surrounding medium 110 and the absorption of EM fields by this surrounding medium 110. Knowing these EM properties makes it possible to adapt the configuration of the radio antenna 103 to optimize the wireless transmission performance of the radio antenna 103 through the surrounding environment. In particular, when the coupling between the radio antenna 103 and the surrounding medium 110 is high, and the transmission properties of the radio antenna can be affected by variations in the EM properties of the surrounding medium 110 in which the biometric device 100 is located.

FIG. 2 schematically represents a geometric configuration of a radio antenna 200 adapted for a biotelemetry device 100 such as that described with reference to FIG. 1, according to an exemplary embodiment.

In one or more embodiments, the radio antenna 200 comprises a substrate 210 formed from a dielectric material (FR4, PFTE, polyimide, polyetheretherketone, ceramics, composites, etc.). The substrate 210 is made either of a flexible material and/or which can be rolled, so as to be able to conform to the interior surface of a biotelemetry device such as a capsule, or of a rigid material suitable for the realization of a planar biotelemetry device. The substrate is for example made of flexible polyimide: such a material is capable of conforming to the internal surface of a capsule of a biotelemetry device.

In one or more embodiments, an electrically conductive ground plane is arranged on a first face F2 (below) of the substrate. The ground plane is for example made of electrically conductive material (for example, metal such as copper, aluminum, silver, etc. or an alloy).

In one or more embodiments, the radio antenna 200 comprises a resonator comprising a first element E1, having a first characteristic impedance Zc-low, and a second element E2, having a second characteristic impedance Zc-high.

In one or more embodiments, the resonator is configured to convert an incident electrical signal produced by the microcontroller into an electromagnetic wave at a resonant frequency dependent on the structural characteristics of the resonator.

The resonant frequency is the frequency for which the imaginary part of the antenna impedance equals zero: $Im(Z_{ANT})=0$.

In one or more embodiments, the first element E1 is configured to receive the incident electrical signal generated by the microcontroller. An electrical supply point is provided at an arbitrary location of the first element. Power can be supplied by microstrip, coaxial cable, or by close coupling.

In one or more embodiments, the first element E1 is formed by a strip of electrically conductive material, the strip being arranged on a second face F1 (top) of the substrate opposite to the first face F2. The material of the ground plane can be identical or different from the material of the strip of conductive material, (for example a metal such as copper, aluminum, silver, etc. or an alloy) The strip of conductive material can have different geometric shapes: a parallelepiped shape, for example rectangular as in the example shown in FIG. 2, a serpentine shape or a zigzag shape, etc.

In one or more embodiments, the second element E2 is formed by a rectilinear segment, cut out in the ground plane, and separated from the rest of the ground plane by a slot 202 of fixed or substantially fixed width, to the tolerances of realization.

In one or more embodiments, the second element E2 is electrically connected to the ground plane at a first end of the straight segment. In one or more embodiments, the second element E2 is electrically connected to the first element E1 at a second end of the rectilinear segment by means of a via 210 passing through the substrate. The first element E1 is thus electrically connected to the ground plane via the via 210 and the second element E2.

In one or more embodiments, the via is connected to an edge of the strip of conductive material. In one or more embodiments, the slot 202 surrounds the via 210 and isolates the via 210 from the ground plane with the exception of the end of the via 210 which is connected to the second end of the straight segment.

In one or more embodiments, the resonator is a quarter wave stepped impedance resonator (SIR) with a transition from low impedance to high impedance and a short circuit in the ground plane at the end of the higher impedance element (high impedance end). This implies an electrical current distribution having its minimum at the end of the element with lower impedance (low impedance end) and its maximum at the end of the element with higher impedance (high impedance end). The voltage distribution is opposite to that of current.

In one or more embodiments, the ratio between the maximum dimension $l_{low}$ along the Y axis of the strip of conductive material and the dimension $l_{high}$ along the Y axis of the straight segment is between 5 and 0.2. The total length of the antenna ($l_{low}+l_{high}$) increasing with the maximum dimension $l_{low}$ along the Y axis of the strip of conductive material, this reduces the miniaturization factor of the antenna.

In one or more embodiments, the rectilinear segment extends longitudinally in a first direction (axis Y in FIG. 2) and the strip of conductive material extends longitudinally in a second direction (axis X in FIG. 2), distinct from the first direction. In one or more embodiments, corresponding to the example illustrated in FIG. 2, the first direction is perpendicular to the second direction or substantially perpendicular to the second direction. In one or more embodiments, the first direction is made at an angle between 0° and 45° with the second direction.

In one or more embodiments, the characteristic impedance Zc-high of the second element E2 is greater than the characteristic impedance Zc-low of the first element E1. In practice, the characteristic impedance Zc-high of the second element E2 depends on the width of the straight segment, on the distance of the straight segment from the ground plane, that is to say the width of the slot 202 and on the electromagnetic and geometric properties of the surrounding materials.

The geometry of the radio antenna satisfying the resonance condition, ie (the resonance frequency corresponds to frequency for which the imaginary part of the antenna impedance is zero: Im ($Z_{ANT}$)=0) can be deduced from the impedance equation for the transmission lines.

In the case of geometric configuration described with reference to FIG. 2, the resonant frequency $f_{res}$ of the radio antenna is related to the dimension $l_{high}$ along the Y axis of the rectilinear segment and the dimension low along the Y axis of the strip of conductive material, to the characteristic impedance Zc-low of first element and the characteristic impedance Zc-high of the second element by the following relationships:

$$-Z_{c-low}+Z_{c-high}\tan(\beta_{high}l_{high})\tan(\beta_{low}l_{low})=0 \quad \text{(eq 1a)}$$

$$Z_{c-high}\tan(\beta_{low}l_{low})+Z_{c-low}\tan(\beta_{high}l_{high})\neq 0 \quad \text{(eq 1b)}$$

$\beta_{low}$ being the phase constant of the first element defined by:

$$\beta_{low}=(2\pi)/cf_{res}\sqrt{\in_{low}^{r,\mathit{eff}}}$$

Where $\beta_{high}$ is the phase constant of the second element defined by $$\beta_{high}=(2\pi)/cf_{res}\sqrt{\in_{high}^{r,\mathit{eff}}}$$

c being the speed of light,
$\in_{high}^{r,\mathit{eff}}$ being the effective relative permittivity of the second element,
$\in_{low}^{r,\mathit{eff}}$ being the effective relative permittivity of the first element.

To design an antenna with a given resonant frequency $f_{res}$, the following procedure can be applied. The total dimension is chosen ($l_{high}+l_{low}$) along the Y axis of the radiofrequency antenna of the radio antenna, for example as a function of the target biotelemetry device. We then choose the maximum useful width $w_{low}$ of the element E1 having the lowest impedance (strip of material). Then, we determine the characteristic impedance $Z_{c-low}$ of the first element and the characteristic impedance $Z_{c-high}$ of the second element as well as the effective relative permittivity of the first element and the effective relative permittivity of the second element by solving the equations (eq1a) and (eq11) above by a numerical method formulated in 2D. The precise dimensions of the elements E1 and E2 can then be finely adjusted using a numerical method formulated in 3D.

One can for example make an antenna at 434 MHz $l_{high}$=4.3 mm, $l_{low}$=4.6 mm, $w_{low}$=20 mm and a slot width 202 of 180 μm.

FIG. 3 schematically represents a biotelemetry device 100 comprising a radio antenna 200 according to the present description in an exemplary embodiment.

The biotelemetry device is in the form of a capsule in which the substrate is integrated so that the face F2 of the substrate on which the ground plane and the rectilinear segment E2 are arranged is turned towards the interior of the capsule and the other face F1 on which the first element E1 is arranged is turned towards the outside of the capsule. The size of the capsule is for example 17.7 mm in length and 8.9 mm in diameter.

In one or more embodiments, the substrate of the radio antenna is a substrate made of flexible material, for example made of flexible polyimide of 50 μm thick, conforming to the internal surface of the capsule.

In one or more embodiments, the substrate is made of a rigid material and of cylindrical shape so as to form a cylindrical radio antenna 200. The dimensions of the substrate and the diameter of the cylinder formed by the substrate are in this case adapted to the internal dimensions of the capsule with a tolerance of 50 μm.

FIG. 4 shows the variation curves of the imaginary part of the impedance (Im ($Z_{ANt}$)) of the radio antenna designed for the ISM band (industrial, scientific and medical) 434 MHz as a function of frequency in an exemplary embodiment. The radio antenna was produced on a printed circuit.

In this embodiment, $l_{high}$=4.3 mm, $l_{low}$=4.6 mm, $w_{low}$=20 mm and a slot width 202 of 180 μm. The operating frequency is 434 MHz.

Curve A (rightmost) corresponds to variations in impedance in air, while curve B (leftmost) corresponds to variations in impedance in a phantom medium equivalent to a muscle of relative permeability 56, 9, conductivity 0.81 S/m at the frequency of 434 MHz.

The point on the curve for which the imaginary part of the impedance is zero gives the resonant frequency of the radio antenna.

In air (curve A), the resonance frequency obtained is 443.8 MHz. In the muscle phantom (curve B), the resonance frequency obtained is 435.1 MHz.

By comparing these resonant frequencies, it can be seen that the resonant frequency only changes by about 2%, which shows the very low sensitivity of the radio antenna's impedance to changes in the environment. This change is very small compared to other radioelectric antennas presenting rates of variation of the resonance frequency of more than 600%, as for example that described in the document entitled "Outer-wall loop antenna for ultrawideband capsule endoscope System" from Yun. S. et al, IEEE Antennas Wireless Propagation Letters, vol. 9 pages 1135-1138, 2010, for which the resonance frequency obtained in air is 2.7 GHz and 434 MHz for the muscle phantom.

The radio antenna described in this document can be designed to operate in a wide range of resonant frequencies, for example between $10^8$ Hz and $5 \times 10^9$ Hz.

The radio antenna described in this document has numerous possibilities of application, whether in the medical or non-medical field, for example, for civil engineering, agriculture, food processing, etc. The radio antenna can be used when high robustness in impedance is required due to variations in the environment in which this radio antenna is intended to be used (for example, the human and/or animal body, but also air, water, clothes, rain, sweat, etc.

One application is its use in an ingestible and/or implantable in vivo biotelemetry device for biotelemetry and teletherapy applications in the human and/or animal body. Another emerging application is the remote monitoring of artificial body models and prostheses.

The invention claimed is:

1. A radio antenna, wherein the radio antenna comprises:
   a substrate formed of a dielectric material;
   a ground plane of electrically conductive material, the ground plane being arranged on a first face of the substrate;
   a resonator configured to convert an incident electrical signal into an electromagnetic wave, the resonator comprising a first element having a first characteristic impedance and a second element having a second characteristic impedance greater than the first characteristic impedance;
   in which
   the first element is configured to receive the incident electrical signal, the first element is formed by a strip of electrically conductive material, the strip being arranged on a second face of the substrate opposite to the first face; and
   the second element is formed by a rectilinear segment, cut out in the ground plane and separated from the rest of the ground plane by a slot of substantially fixed width, the second element is electrically connected to the ground plane at a first end of the rectilinear segment and electrically connected to the first element at a second end of the rectilinear segment by means of a via passing through the substrate,
   in which the rectilinear segment is oriented in a first direction and a strip of the conductive material extends longitudinally in a second direction distinct from the first direction, and
   in which a resonance frequency $f_{res}$ of the radio antenna is related to a dimension $l_{high}$ according to the first direction of the rectilinear segment and a dimension $l_{low}$ along the first direction of the strip of the conductive material, to a characteristic impedance $Z_{c\text{-}low}$ of the first element and to a characteristic impedance $Z_{c\text{-}high}$ of the second element by the relations:

$$-Z_{c\text{-}low} + Z_{c\text{-}high} \tan(\beta_{high} l_{high}) \tan(\beta_{low} l_{low}) = 0$$

$$Z_{c\text{-}high} \tan(\beta_{low} l_{low}) + Z_{c\text{-}low} \tan(\beta_{high} l_{high}) \neq 0$$

$\beta_{low}$ being a phase constant of the first element defined by:

$$\beta_{low} = (2\pi)/cf_{res}\sqrt{\in_{low}^{r,\mathit{eff}}}$$

where $\beta_{high}$ is a phase constant of the second element defined by $$\beta_{high} = (2\pi)/cf_{res}\sqrt{\in_{high}^{r,\mathit{eff}}}$$

c being the speed of light,
   $\in_{high}^{r,\mathit{eff}}$ being an effective relative permittivity of the second element,
   $\in_{low}^{r,\mathit{eff}}$ being an effective relative permittivity of the first element.

2. Radio antenna according to claim 1, wherein the first direction is substantially perpendicular to the second direction.

3. Radio antenna according to claim 1, in which the strip of the conductive material is of parallelepiped, serpentine or zigzag shape.

4. Radio antenna according to claim 1, in which a ratio between a maximum width of the strip of the conductive material and a width of the rectilinear segment is between 5 and 0.2.

5. Biotelemetry device comprising a radio antenna according to claim 1.

6. Biotelemetry device according to claim 5, in which the substrate is in a flexible material and the biotelemetry device is in the form of a capsule in which the substrate is rolled so that the first face of the substrate is turned towards the inside of the capsule and the second face faces the outside of the capsule.

7. Biotelemetry device according to claim 5, in which the substrate is made of a rigid material and of cylindrical shape, the biotelemetry device being integrated in a capsule wherein the radioelectric antenna is placed so that the first face of the substrate is turned towards the interior of the capsule and the second face is turned towards the outside of the capsule.

8. Biotelemetry device according to claim 6, in which the substrate of the radio antenna is a flexible polyimide substrate conforming to an internal surface of the capsule.

9. Biotelemetry device comprising a radio antenna,
   wherein the radio antenna comprises:
   a substrate formed of a dielectric material;
   a ground plane of electrically conductive material, the ground plane being arranged on a first face of the substrate;
   a resonator configured to convert an incident electrical signal into an electromagnetic wave, the resonator comprising a first element having a first characteristic impedance and a second element having a second characteristic impedance greater than the first characteristic impedance;

in which
the first element is configured to receive the incident electrical signal, the first element is formed by a strip of electrically conductive material, the strip being arranged on a second face of the substrate opposite to the first face;
the second element is formed by a rectilinear segment, cut out in the ground plane and separated from the rest of the ground plane by a slot of substantially fixed width, the second element is electrically connected to the ground plane at a first end of the rectilinear segment and electrically connected to the first element at a second end of the rectilinear segment by means of a via passing through the substrate; and
the substrate is in a flexible material and the biotelemetry device is in the form of a capsule in which the substrate is rolled so that the first face of the substrate is turned towards the inside of the capsule and the second face faces the outside of the capsule.

10. Biotelemetry device according to claim 9, in which the substrate of the radio antenna is a flexible polyimide substrate conforming to an internal surface of the capsule.

11. Biotelemetry device according to claim 9, wherein the rectilinear segment is oriented in a first direction and the strip of the conductive material extends longitudinally in a second direction distinct from the first direction.

12. Biotelemetry device according to claim 11, wherein the first direction is substantially perpendicular to the second direction.

13. Biotelemetry device according to claim 9, in which the strip of the conductive material is of parallelepiped, serpentine or zigzag shape.

14. Biotelemetry device according to claim 9, in which a ratio between a maximum width of the strip of conductive material and a width of the rectilinear segment is between 5 and 0.2.

15. Biotelemetry device comprising a radio antenna, wherein the radio antenna comprises:
a substrate formed of a dielectric material;
a ground plane of electrically conductive material, the ground plane being arranged on a first face of the substrate;
a resonator configured to convert an incident electrical signal into an electromagnetic wave, the resonator comprising a first element having a first characteristic impedance and a second element having a second characteristic impedance greater than the first characteristic impedance;
in which
the first element is configured to receive the incident electrical signal, the first element is formed by a strip of electrically conductive material, the strip being arranged on a second face of the substrate opposite to the first face;
the second element is formed by a rectilinear segment, cut out in the ground plane and separated from the rest of the ground plane by a slot of substantially fixed width, the second element is electrically connected to the ground plane at a first end of the rectilinear segment and electrically connected to the first element at a second end of the rectilinear segment by means of a via passing through the substrate; and
the substrate is made of a rigid material and of cylindrical shape, the biotelemetry device being integrated in a capsule wherein the radioelectric antenna is placed so that the first face of the substrate is turned towards the interior of the capsule and the second face is turned towards the outside of the capsule.

16. Biotelemetry device according to claim 15, wherein the rectilinear segment is oriented in a first direction and the strip of the conductive material extends longitudinally in a second direction distinct from the first direction.

17. Biotelemetry device according to claim 16, wherein the first direction is substantially perpendicular to the second direction.

18. Biotelemetry device according to claim 15, wherein the strip of the conductive material is of parallelepiped, serpentine or zigzag shape.

19. Biotelemetry device according to claim 15, wherein a ratio between a maximum width of the strip of the conductive material and a width of the rectilinear segment is between 5 and 0.2.

* * * * *